United States Patent [19]

Schroeder et al.

[11] Patent Number: 5,270,186

[45] Date of Patent: Dec. 14, 1993

[54] ANTITUMOR ANTIBIOTIC BMY-42448

[75] Inventors: Daniel R. Schroeder, Higganum; Kin S. Lam, Cheshire; Grace A. Hesler, Branford; Donald R. Gustavson, Torrington, all of Conn.; Koji Tomita, Tokyo, Japan; Ronald L. Berry, North Branford, Conn.

[73] Assignee: Bristol-Myers Squibb Company, New York, N.Y.

[21] Appl. No.: 776,526

[22] Filed: Oct. 10, 1991

Related U.S. Application Data

[62] Division of Ser. No. 463,220, Jan. 10, 1990, Pat. No. 5,082,933.

[51] Int. Cl.$^5$ ............................................. C12P 19/02
[52] U.S. Cl. ............................... 435/105; 536/16.8
[58] Field of Search ..................... 435/105; 536/16.8

[56] References Cited

U.S. PATENT DOCUMENTS 4,162,305  7/1979  Nara et al. .................... 435/867
4,275,155  6/1981  Pereira Da Luz ................ 435/80

OTHER PUBLICATIONS

Tomita F. et al., J. Antibiot., 33, 668,940,946 (1980).
Waitz, J. A. et al., J. Antibiotics, 34, 1101 (1981).
Mallams, A. K. et al., J. Am. Chem. Soc. 103,2938,3940 (1981).
Mantwyler, R. et al., Helv. Chem. Acta, 55,2071 (1972).

Primary Examiner—Ronald W. Griffin
Assistant Examiner—Pamela S. Webber
Attorney, Agent, or Firm—Mollie M. Yang

[57] ABSTRACT

An antibiotic designated BMY-42448 is produced by fermentation of *Micromonospora narashinoensis* strain C39217-R109-7 (ATCC-53791). BMY-42448 exhibits both in vitro and in vivo antitumor activity.

1 Claim, No Drawings ns as ATCC-53791. The culture is also maintained as a dormant culture in lyophile tubes and cryogenic vials in the Bristol-Myers Pharmaceutical Research and Development Division Culture Collection, 5 Research Parkway, Wallingford, Conn. 06492.

ANTITUMOR ANTIBIOTIC BMY-42448

CROSS REFERENCE TO RELATED APPLICATIONS

This is a divisional of our copending application U.S. Ser. No. 07/463,220 filed Jan. 10, 1990, now U.S. Pat. No. 5,082,933.

BACKGROUND OF THE INVENTION

1. Field of the Invention

This invention relates to a new antibiotic designated herein as BMY-42448 and to its use as an antitumor agent. The invention also relates to production of BMY-42448 by fermentation of a new strain of Micromonospora.

2. Description of the Prior Art

On the basis of the physico-chemical properties of a purified sample of BMY-42448, the structure of the compound has been elucidated except for the absolute stereochemistry.

BMY-42448 is classified by the CRC Handbook of Antibiotic Compounds as a condensed macrolactone. It has the unique structural feature of a 13-membered macrolide in which a spiro-α-acyltetronic acid moiety constitutes the lactone group. Two other examples of antibiotics possessing this distinctive arrangement in the core of their aglycones have been reported (tetrocarcins; Tomita, F. et al, J. Antibiot., 33, 668, 940 (1980) and kijanimicin; Waitz, J.A. et al. J. Antibiotics, 34, 1101 (1981); Mallams, A.K. et al, J. Am. Chem. Soc., 103, 3938, 3940 (1981)). A third closely related group of antibiotics, but possessing an additional oxygen in the macrolactone ring, is exemplified by chlorothricin; Muntwyler, R. et al., Helv. Chem. Acta, 55, 2071 (1972). All of the above materials differ from BMY-42448 in both sugar sidechains and by substitution on the aglycone portion, thus establishing BMY-42448 as a novel antibiotic.

SUMMARY OF THE INVENTION

There is provided by the present invention a new antibiotic designated herein as BMY-42448, said antibiotic being produced by cultivating a BMY-42448-producing strain of Micromonospora narashinoensis, most preferably Micromonospora narashinoensis strain C39217-R109-7 (ATCC-53791) or a mutant or variant thereof in an aqueous nutrient medium containing assimilable sources of carbon and nitrogen under submerged aerobic conditions until a substantial amount of BMY-42448 is produced by said organism in said culture medium. The BMY-42448 so obtained may be isolated from the fermentation medium in substantially pure form by conventional procedures. BMY-42448 exhibits antitumor activity in standard antitumor animal model systems.

DETAILED DESCRIPTION

The BMY-42448 antibiotic of the present invention may be prepared by fermentation of a BMY-42448-producing strain of Micromonospora. The preferred producing organism is a novel strain of Micromonospora designated herein as Micromonospora strain C39217-R109-7. This organism was isolated from a soil sample collected at Puerto Viejo, Peru. A biologically pure culture of strain C39217-R109-7 has been deposited with the American Type Culture Collection, Rockville, Md. and added to its permanent collection of microorganisms as ATCC-53791. The culture is also maintained as a dormant culture in lyophile tubes and cryogenic vials in the Bristol-Myers Pharmaceutical Research and Development Division Culture Collection, 5 Research Parkway, Wallingford, Conn. 06492.

The results of taxonomic studies performed on strain C39217-R109-7 indicate that the strain is a novel strain of Micromonospora. Based on the characteristics indicated below, strain C39217-R109-7 is believed to belong to the species group of Micromonospora narashinoensis.

Macroscopic cultural characteristics of the actinomycete strain C39217-R109-7 were observed after a 14 day incubation period at 28° C. on various media. Slant cultures were observed further at one week intervals for a two month period. Characteristics of strain C39217-R109-7 are summarized in Table 1.

Utilization of carbon sources was tested according to the method of Shirling and Gottlieb (Int. J. Syst. Bacteriol. 16:3132–3140, 1966) and results appear in Table 2. Physiological characteristics are summarized in Tables 3 and 4.

Analysis of whole cell hydrolyzates was performed according to the methods of K.P. Schaal (Chemical Methods in Bacterial Systematics, Eds., Goodfellow and Minnikin, pgs. 359–381, Academic Press, Inc., Orlando, Fla., 1985). Strain C39217-R109-7 contains meso-diaminopimelic acid, xylose, glucose and mannose. Phosphatidyl ethanolamine was the only phospholipid detected by the method of Lechevalier and Lechevalier (Actinomycete Taxonomy, Soc. for Industrial Microbiology Special Publication No. 6, Ed., A. Dietz and D.W. Thayer, pgs. 227–291, Virginia, 1980). Strain C39217-R109-7 was assigned cell wall Type IID with a PII phospholipid pattern, consistent with members of the genus Micromonospora.

Macroscopic examination of strain C39217-R109-7 revealed a fine branched vegetative mycelium bearing monospores. Examination of broth cultures shows fragments of hyphae bearing spores in clusters. Also observed were irregular globose structures resembling those described in the Kriss (Mikrobiologiya 8:178–185, 1939) description of Micromonospora globosa.

As presented in Table 5, strain C39217-R109-7 has properties resembling both Micromonospora globosa and Micromonospora narashinoensis. Since the irregular swelling structures have been reported in species other than M. globosa (Luedemann, George M., Adv. Appl. Microbiol. 11:101–133, Academic Press Inc., New York, 1969), it is believed that strain C39217-R109-7 represents a new strain of Micromonospora narashinoensis.

TABLE 1

| Cultural Characteristics of strain 39217-R109-7 | | |
|---|---|---|
| ISP Medium 1 | G: | Moderate, orange, floccose |
| ISP Medium 2 | G: | Moderate, raised |
|  |  | (38), dark reddish orange |
|  | R: | (38) |
|  | AM: | None |
|  | SP: | None |
| ISP Medium 3 | G: | Fair, (26), strong yellowish pink |
|  | R: | (26), strong yellowish pink |
|  | AM: | None |
|  | SP: | None |
| ISP Medium 4 | G: | Poor, (27), deep yellowish pink |
|  | R: | (30), dark yellowish pink |
|  | AM: | scant, pink |
|  | SP: | None |
| ISP Medium 5 | G: | Fair, raised; (36), deep reddish orange |
|  | R: | (36), deep reddish orange |

TABLE 1-continued

Cultural Characteristics of strain 39217-R109-7

| | | |
|---|---|---|
| ISP Medium 6 | AM: | scant, pink |
| | SP: | None |
| | G: | Poor |
| | R: | (29), medium yellowish pink |
| | AM: | None |
| | SP: | None |
| ISP Medium 7 | G: | Fair, (30), dark yellowish pink |
| | R: | (42), light reddish brown |
| | AM: | None |
| | SP: | (33), bright pink |
| Glucose-Asparagine Agar | G: | Fair, (37), medium reddish orange |
| | R: | (29), medium yellowish pink |
| | AM: | None |
| | SP: | None |
| Czapek's Sucrose-Nitrate Agar | G: | Scant, (37), medium reddish orange |
| | R: | (39), grayish reddish orange |
| | AM: | None |
| | SP: | None |

Color names and numbers from the ISCC-NBS Color-Name Charts, Publication 440, Washington, D.C., 1976
G: Growth, R: Reverse, AM: Aerial mycelium, SP: Soluble pigment

TABLE 2

Utilization of carbon sources by Strain 39217-R109-7

Positive Utilization
- Glucose
- Cellobiose
- Rhamnose
- Trehalose
- Potato starch

Moderate Utilization
- Glycerol
- Ribose

Negative Utilization

| | |
|---|---|
| Mannitol | Sucrose |
| Mannose | Maltose |
| Fructose | Sorbose |
| Galactose | Melezitose |
| Lactose | Melibiose |
| L-arabinose | Salicin |
| D-arabinose | Dulcitol |
| Raffinose | Cellulose |
| Xylose | Inositol |

TABLE 3

Physiological Properties of strain 39217-R109-7

| | |
|---|---|
| Growth Temperature | 22-42° C. |
| NaCl Tolerance | 1 to 3% (+), 4% (−) |
| Starch Hydrolysis | (+) |
| Gelatin Liquefaction | (+) |
| Milk Coagulation | (+) |
| Milk Peptonization | (+) |
| Nitrate Reduction | (+) |
| Tyrosinase Reaction | weak |
| $H_2S$ Production | (−) |

TABLE 4

$^a$API ZYM results: Strain 39217-R109-7

| | |
|---|---|
| Alkaline Phosphatase | +++ |
| Esterase | + |
| Esterase-Lipase | + |
| Lipase | +− |
| Leucine amino-peptidase | +++ |
| Valine amino-peptidase | +++ |
| Cystine amino-peptidase | +− |
| Trypsin | +− |
| Chymotrypsin | + |
| Acid phosphatase | +++ |
| Phosphohydrolase | +++ |
| α galactosidase | − |
| β galactosidase | − |
| β glucuronidase | − |
| α glucosidase | − |
| β glucosidase | ++ |
| N-acetyl-β-glucosaminidase | +− |
| α mannosidase | − |
| α fucosidase | − |

$^a$API Analytab Products, Division of Sherwood Medical, 200 Express Street, Plainview, N.Y. 11803; semi-quantitative system for detection of enzyme activities (see J. Clin. Pathol. 30:275-277, 1977).

TABLE 5

**Comparison of strain 39217-R109-7 with published descriptions of *Micromonospora globosa* and *Micromonospora narashinoensis***

| Cultural characteristics | C39217-R109-7 | M. globosa | M. narashinoensis |
|---|---|---|---|
| Colony color | pink-orange to orange | pale yellow to red-orange | orange, |
| texture | plicate | leathery, becoming plicate (2 wks) | folded |
| Spore morphology | monospores, irregular swellings and bulbs | monospores 1-3 μm, irregular swellings and bulbs | Spherical or elongate monospores, 0.6-1.0 μm by 0.9-1.8 μm |
| Temp range for growth | 22-42° C. | Unable to grow at 45° C. | Not available |
| Nutrient agar | minute, tan | deep orange with pale orange-yellow pigment | minute, orange to tan colonies; spore layer at periphery |
| Tyrosine agar | minute, pale orange; pink/purple pigment | pale orange-yellow; no pigment | minute, orange colonies; purplish pigment |
| Starch hydrolysis | positive | positive (under colonies only) | positive |
| Nitrate reduction | positive | positive (Gilkey's) | negative |
| Gelatin liquefaction | positive | variable | positive |
| Milk | rapidly digested | slowly peptonized | digested |

It is to be understood that for the production of BMY-42448, the present invention, though described in detail with reference to the particular strain *Micromonospora narashinoensis* strain C39217-R109-7, is not limited to this microorganism or to organisms fully described by the cultural characteristics disclosed herein. It is specifically intended that the invention embrace strain C39217-R109-7 and all BMY-42448-producing variants and mutants thereof which may be obtained by methods well-known to those skilled in the art, e.g. by subjecting the deposited microorganism to x-ray or ultraviolet radiation, nitrogen mustard, phage exposure, or the like.

The BMY-42448 antibiotic of the present invention is prepared by cultivating a BMY-42448-producing strain of *Micromonospora narashinoensis*, preferably a strain having the identifying characteristics of strain C39217-R109-7 (ATCC-53791) or a BMY-42448-producing mutant or variant thereof, in a conventional aqueous nutrient medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for cultivation of other actinomycetes are applicable to the present invention.

The organism is grown in a nutrient medium containing an assimilable carbon source such as glucose, cellobiose, trehalose, potato starch, glycerol or ribose. The medium should also contain an assimilable nitrogen source such as fishmeal, peptone, peanut meal, cottonseed meal or cornsteep liquor. Nutrient inorganic salts can also be incorporated in the medium so as to provide sodium, potassium, ammonium, calcium, phosphate, nitrate, chloride, bromide, carbonate and like ions. Trace elements such as copper, manganese, iron, zinc, etc. are added to the medium if desired, or they may be present as impurities of other constituents of the media.

Production of BMY-42448 can be effected at any temperature conducive to satisfactory growth of the producing organism, e.g. 22° to 42° C., and is conveniently carried out at a temperature of about 28° C. The fermentation may be carried out in flasks or in laboratory or industrial fermentors of various capacity. When tank fermentation is to be used, it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of BMY-42448. The medium in which the vegetative inoculum is prepared can be the same as, or different from, that used in the tank as long as it is such that a good growth of the producing organism is obtained. Further agitation may be provided by a mechanical impeller. Antifoam agents such as lard oil or silicone oil may also be added if needed. Antibiotic production may be monitored by high performance liquid chromatography (HPLC) assay or by a conventional biological assay.

When the fermentation is complete, the BMY-42448 antibiotic is extracted from the culture broth with a suitable organic solvent and the antibiotic recovered from the extract and purified by conventional isolation procedures such as those described in Example 5 below.

Physico-chemical Properties

A purified sample of BMY-42448 was isolated as a white solid. Characterizing properties of the antibiotic are shown below.

Molecular formula: $C_{44}H_{54}Cl_2N_2O_{10}$

Infrared spectrum: Perkin-Elmer 1800 FTIR Spectrometer, Thin film, $cm^{-1}$: 3410, 3145, 3040, 2970, 2940, 2255, 1765, 1700, 1620, 1560, 1532, 1445, 1420, 1382, 1330, 1245, 1174, 1075, 1015, 980, 915, 870, 792, 738.

Ultraviolet spectrum: Hewlett Packard 8452A Diode Array Spectrophotometer; concentration 1.0 mg/100 ml $CH_3OH$. A neutral solution of sample gave the following absorption maximum: $\lambda_{max}$ nm ($E_{1cm}^{1\%}$):268 (341).

Mass spectrum: Kratos MS50 TC mass spectrophotometer.

FABMS: 879.2783 ($M+K^+$)

$^{13}C$-NMR (90 MHz): Bruker AM 500 spectrometer with Aspect 3000 diode array processor. Broad band probe, 5 mm. Solvent: $d_6$-DMSO. Observed chemical shifts (ppm): 204.9, 197.5, 167.8, 166.0, 158.9, 140.8, 134.1, 132.3, 131.4, 131.2, 131.1, 128.2, 124.3, 122.0, 116.8, 112.3, 108.0, 103.8, 101.3, 85.0, 84.9, 70.7, 67.9, 58.0, 54.5, 43.3, 41.6, 40.3, 39.6, 38.0, 36.0, 35.6, 34.2, 33.7, 31.7, 30.1, 26.1, 24.1, 22.4, 22.2, 18.4, 13.2, 12.9, 11.6.

$^1H$-NMR (300 MHz): Bruker Model AM-3000 Spectrometer. Dual carbon-proton probe, 5 mm. Solvent: $d_6$-DMSO Observed chemical shifts (ppm): 12.52 (br S, 2H), 7.05 (br S, 1H), 6.62 (S, 1H), 6.25 (d, 1H), 5.67 (m, 1H), 5.58 (d, 1H), 5.50 (m, 1H), 5.31 (d, 1H), 5.24 (m, 1H), 5.10 (m, 1H), 4.90 (br S, 1H), 4.43 (d, 1H), 3.60 (m, 1H), 3.42 (m, 1H), 3.33 (m, 2H), 2.79 (m, 1H), 2.60 (m, 2H), 2.48 (m, 3H), 2.29 (m, 1H), 2.12 (br d, 1H), 2.04 (br d, 1H), 1.91 (m, 2H), 1.73 (m, 3H), 1.68 (m, 1H), 1.62 (m, 1H), 1.52 (m, 2H), 1.40 (m, 2H), 1.25 (m, 1H), 1.21 (s, 3H), 1.08 (d, 3H), 0.94 (d, 3H), 0.83 (t, 6H).

On the basis of the physico-chemical properties of BMY-42448, the structure has been determined to be as shown below:

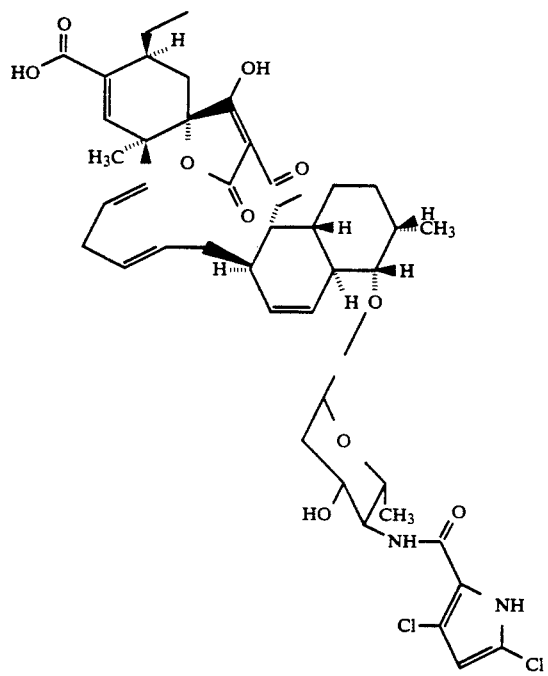

Biological Properties

BMY-42448 was evaluated in vitro on two cancer cell lines, a murine melanoma line labeled B-16 and a human colon cancer cell line termed HCT-116.

The test procedure is as follows:

Culture media consists of McCoy's 5A media, 10% heat inactivated fetal bovine serum and 0.0223 molar Hepes buffer. A 150 μl aliquot of culture media containing 3750 cells was plated into each well of a 96 well microtiter plate on day 0 and allowed to attach by incubation for 24 hours at 37° C. in a 5% carbon dioxide atmosphere. Drugs were then added to the top row of the wells and serially diluted down the plate (except for the untreated control column on each plate). The cells and drug were incubated together as above for 3 days. Following incubation, dead unattached cells and media were removed by inverting the plate. Cells that are undamaged by the drug remain attached to the plate. Cells remaining in the wells were fixed for 10 minutes with 100 μl per well of 3.7% formaldehyde Hank's balanced salt solution. The fixing solution was removed by inverting the plate and the plates were air-dried. Remaining cells are visualized by adding 55 μl of 0.0075% crystal violet (a protein stain), rinsing twice after 15 minutes and quantitating the amount of protein stain in each well. This allows the calculation of the $IC_{50}$ value (drug concentration at which cell growth is inhibited by 50%) for the test compound and reference drugs. The results obtained for BMY-42448 are shown in the table below:

| Drug | In vitro cytotoxicity ($IC_{50}$ in μg/ml) | |
|---|---|---|
| | B-16 melanoma | HCT-116 colon |
| BMY-42448 | 16 | 0.25 |
| Cisplatin | 15.6 | 3.9 |
| Mitomycin C | 0.98 | 0.25 |

The above results indicate that the activity of BMY-42448 on the B-16 melanoma cell line was equal to that of cisplatin and on the HCT-116 colon cancer line was equivalent to that of mitomycin C.

BMY-42448 was also tested in vivo in the P388 murine leukemia model. When $1 \times 10^6$ leukemia cells are implanted ip into $CDF_1$ female mice, the median survival time for untreated controls was 10 days. Mice treated with 135 mg/kg once a day for 5 days beginning 1 day after tumor implant died of drug toxicity. Mice treated with 45 or 15 mg/kg BMY-42448 on the same schedule had median survival time of 13.5 and 13 days, respectively. Each drug treatment group consisted of 4 mice. The positive control reference drug, olivomycin A, was dosed at 0.4 and 0.2 mg/kg once a day for 5 days beginning one day after implant, with median survival times of 16.5 and 16 days, respectively. Both drugs were administered via the intraperitoneal route. Thus, BMY-42448 was active in the ip/ip P388 model with a maximum tolerated dose of 45 mg/kg.

BMY-42448 was tested in an iv-implanted P388 tumor model. In this model $1 \times 10^6$ cells are implanted intravenously in $CDF_1$ female mice. The untreated control group had a median survival time of 8 days. Mitomycin C given iv once at 3.2 mg/kg on the day after tumor implant extended median survival to 12 days after tumor implant. BMY-42448 was toxic when administered iv at 10 mg/kg every other day for 3 doses beginning one day after tumor implant. At doses of 5, 2.5 or 1.25 mg/kg given on the same schedule, BMY-42448 was inactive at all doses with the median life span being 8 days for each treatment group of 6 animals.

Therapeutic Use

As indicated above BMY-42448 has been found to possess both in vitro and in vivo antitumor activity in standard tests.

In one aspect then, the present invention provides a method of treating a mammalian host affected by a malignant tumor sensitive to BMY-42448 which comprises administering to said host a tumor-inhibiting dose of BMY-42448 or a pharmaceutical composition thereof.

In another aspect the present invention provides pharmaceutical compositions comprising an effective tumor-inhibiting amount of BMY-42448 in combination with an inert pharmaceutically acceptable carrier or diluent. Such compositions may contain other antitumor agents and may be made up in any form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral administration such as sterile solutions, suspensions or emulsions. They may also be manufactured in the form of sterile solid compositions which can be dissolved in sterile water, physiological saline or some other sterile injectable medium immediately before use.

Optimal dosages and regimens of BMY-42448 for a given mammalian host can be readily ascertained by those skilled in the art. It will of course be appreciated that the actual dose of BMY-42448 used will vary according to the particular compositon formulated, the mode of application and the particular situs, host and disease being treated. Many factors that modify the action of the drug will be taken into account including age, sex, weight, diet, time of administration, route of administration, rate of excretion, conditon of the patient, drug combinations, reaction sensitivities and severity of the disease.

The following examples are not intended to be limiting but are illustrative of the invention. Unless otherwise indicated, all solvent ratios and percentages are by volume.

EXAMPLE 1

Preparation of Cryopreserved Culture of Micromonospora Strain C39217-R109-7

Micromonospora strain C39217-R109-7 was maintained as a cryopreserved culture stored at −80° C. in a Revco ultralow temperature freezer. To prepare a cryopreserved culture, strain C39217-R109-7 was cultured in test tubes on slants of yeast-malt extract agar supplemented with $CaCO_3$ which consisted of:

| | |
|---|---|
| dextrose | 4.0 g |
| yeast extract | 4.0 g |
| malt extract | 10 g |
| $CaCO_3$ | 1.5 g |
| agar | 15 g |
| deionized water | q.s. to 1 liter |

The agar slant was incubated at 28° C. for 7–10 days. Vegetative culture was prepared by transferring the surface growth aseptically from the slant culture to a 500 ml Erlenmeyer flask containing 100 ml of a sterile vegetative medium consisting of:

| | |
|---|---|
| Staclipse J-UB starch (A. E. Staley) | 20 g |
| Cerelose (Corn Products) | 5 g |
| Pharmamedia (Traders Oil Mill Co.) | 10 g |
| Debittered Brewer's yeast | 10 g |
| $CaCO_3$ | 2 g |
| deionized water | q.s. to 1 liter |

This vegetative culture was incubated at 28° C. for 72 hours on a rotary shaker set at 250 rev/min. The vegetative culture was mixed with equal volume of cryoprotective solution consisting of:

| | |
|---|---|
| sucrose | 100 g |
| glycerol | 200 g |
| deionized water | q.s. to 1 liter |

Four ml portions of this mixture were transferred to sterile cryogenic tubes (5 ml capacity, Corning) and were frozen in a dry ice-acetone bath. The frozen vegetative cultures were then stored at −80° C. in a Revco ultralow temperature freezer.

EXAMPLE 2

Preparation of Vegetative Culture of Micromonospora Strain C39217-R109-7

Vegetative culture was prepared by transferring 4 ml of the cryopreserved culture to a 500 ml Erlenmeyer flask containing 100 ml of a sterile vegetative medium having the same composition as the cryopreserved vegetative culture. C39217-R109-7 was incubated at 28° C. for 72 hours on a rotary shaker set at 250 rev/min.

EXAMPLE 3

Fermentation of BMY-42448 in shake flask culture

Four ml of the vegetative culture of Example 2 was inoculated into 500 ml Erlenmeyer flasks each containing 100 ml of a production medium consisting of:

| | |
|---|---|
| Staclipse J-UB starch (A. E. Staley) | 30 g |
| Bacto-liver (Difco) | 10 g |
| Pharmamedia (Traders Oil Mill Co.) | 5 g |
| NaCl | 3 g |
| $(NH_4)_2SO_4$ | 1 g |
| $CaCO_3$ | 6 g |
| deionized water | q.s. to 1 liter |

The production culture was incubated at 28° C. on a rotary shaker set at 250 rev/min. The production of BMY-42448 was monitored by HPLC analysis. Optimal production of 389-468 mcg/ml was generally reached at 6-7 days of fermentation.

EXAMPLE 4

Fermentation of BMY-42448 in fermentor culture

A vegetative culture (100 ml) was prepared as described in Example 2. Twenty-five ml of the vegetative culture were transferred into a 2 L Erlenmeyer flask containing 500 ml of the same vegetative medium. Three vegetative cultures were prepared and incubated at 28° C. for 72 hours on a rotary shaker (250 rev/min). The resulting cultures were combined and inoculated aseptically into a Biolafitte fermentor (50 L nominal volume) containing 30 L of production medium as described in Example 3. The fermentation was carried out at 28° C., aeration of 0.7 volume per minute and the agitation set at 250 rev/min. BMY-42448 production reached a maximum titer of 157-340 mcg/ml at 6-7 days of fermentation according to HPLC analysis.

EXAMPLE 5

Isolation and Purification of BMY-42448

A. Extraction

Acetone (1 L) was added to 10 L of whole fermentation broth prepared according to the general procedures of Examples 3-4. After standing for one hour, ethyl acetate (4 L) was mixed in resulting in the formation of two layers. Upon evaporation under reduced pressure, the top layer yielded 630 mg of crude extract.

B. Solvent Partitioning (Kupchan Distribution)

The Kupchan distribution was carried out as follows: Crude extract (from Part A of Example 5) (220 mg) was dissolved in 10% aqueous methanol (100 ml) and partitioned against hexanes (100 ml, presaturated with 10% aqueous $CH_3OH$) in a 500 ml separatory funnel. The layers were separated and the aqueous methanol layer (bottom) washed an additional two times with fresh hexanes. The combined hexane layers were concentrated in vacuo to yield 49 mg residue.

Water (20 ml) was added to the aqueous methanol layer to yield 120 ml of 25% aqueous $CH_3OH$. This layer was further partitioned against 120 ml of carbon tetrachloride (presaturated with 25% aqueous $CH_3OH$) and the layers separated. Two additional washes of the aqueous methanol with carbon tetrachloride yielded 43 mg residue upon concentration of the combined organic layers.

More water (20 ml) was added to the aqueous methanol to yield 140 ml of 35% aqueous $CH_3OH$. This was partitioned against chloroform (140 ml, presaturated with 35% aqueous $CH_3OH$ and the layers separated. The bottom layer, when combined with two additional chloroform washes (as above) yielded 86 mg residue upon removal of solvent under reduced pressure.

Evaporation of the residual 35% aqueous methanol layer resulted in a fourth residue (25 mg).

C. Size Exclusion Chromatography

The carbon tetrachloride and chloroform residues (125 mg) from the Kupchan distribution experiment were combined in 2 ml of chloroform: methanol (1:1) and applied to a Glenco column (2.5 I.D.×100 cm) containing 140 g of Sephadex LH-20 preswollen in $CHCl_3:CH_3OH$ (1:1). A flow rate of 1.5 ml/min was maintained. After a 90 ml void volume, twenty 15 ml tubes were collected, followed by a 500 ml wash volume of the same eluant. TLC analysis indicated a major UV quenching (254 nm) zone in tubes 9-11 (one-half bed volume) which gave a purple color with vanillin spray reagent and heating. These tubes were combined and concentrated to yield 52 mg of residue.

D. HPLC Purification

The 52 mg residue from step (c) was dissolved in 0.5 ml DMSO and injected onto a Whatman RF-C18 column [Partisil 10 ODS-3 (50 cm×10 mm)] equilibrated with 0.1M ammonium acetate:methanol:tetrahydrofuran (50:25:25)-flow rate 4.0 ml/min.; detection at 254 nm. The material of interest eluted in 20.5 minutes over two fractions. These fractions were pooled, extracted with two 25 ml volumes of chloroform, and the combined organic layers concentrated to dryness to yield BMY-42448 (16.7 mg) as a white solid.

We claim:

1. A process for producing the antibiotic BMY-42448 having the formula which comprises cultivating a BMY-42448-producing strain of *Micromonospora narashinoensis*, said strain having the identifying characteristics of Strain C39217-R109-7 (ATCC-53791), or a BMY-42448-producing mutant or variant thereof, in an aqueous nutrient medium containing assimilable sources of carbon and nitrogen under submerged aerobic conditions until a substantial amoung of BMY-42448 is produced by said organism in said culture medium and then recovering the BMY-42448 from the culture medium.

* * * * *

UNITED STATES PATENT AND TRADEMARK OFFICE
CERTIFICATE OF CORRECTION

PATENT NO. : 5,270,186
DATED : Dec. 14, 1993
INVENTOR(S) : Daniel R. Schroeder, et al It is certified that error appears in the above-indentified patent and that said Letters Patent is hereby corrected as shown below:

Column 1, claim 1, the structure should read as follows:

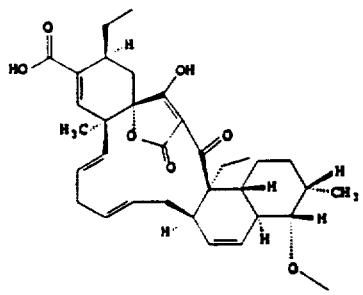

Signed and Sealed this

Fifth Day of July, 1994

Attest:

Attesting Officer

BRUCE LEHMAN

Commissioner of Patents and Trademarks